United States Patent [19]

Leone

[11] Patent Number: 5,797,868
[45] Date of Patent: Aug. 25, 1998

[54] PHOTODYNAMIC THERAPY BALLOON CATHETER

[75] Inventor: James E. Leone, Miami, Fla.

[73] Assignee: Cordis Corporation, Miami Lakes, Fla.

[21] Appl. No.: 690,329

[22] Filed: Jul. 25, 1996

[51] Int. Cl.⁶ ..................................... A61N 1/30
[52] U.S. Cl. .................. 604/21; 604/96; 606/15; 607/89
[58] Field of Search ................. 604/19–21, 49, 604/96; 606/7, 8, 13–17; 607/80, 88, 89; 128/633, 634

[56] References Cited

U.S. PATENT DOCUMENTS

| | | |
|---|---|---|
| 4,636,195 | 1/1987 | Wolinsky. |
| 4,878,492 | 11/1989 | Sinofsky et al. ............ 606/7 |
| 5,047,028 | 9/1991 | Qian. |
| 5,049,132 | 9/1991 | Shaffer et al.. |
| 5,087,243 | 2/1992 | Avitall. |
| 5,169,395 | 12/1992 | Narciso, Jr. .............. 606/14 |
| 5,209,748 | 5/1993 | Daikuzono ............... 606/7 |
| 5,213,576 | 5/1993 | Abiuso et al.. |
| 5,236,413 | 8/1993 | Feiring. |
| 5,286,254 | 2/1994 | Shapland et al.. |
| 5,303,324 | 4/1994 | Lundahl .................. 606/7 |
| 5,318,531 | 6/1994 | Leone. |
| 5,405,472 | 4/1995 | Leone. |
| 5,505,700 | 4/1996 | Leone et al.. |

FOREIGN PATENT DOCUMENTS

| | | |
|---|---|---|
| 2154761 | 9/1985 | United Kingdom. |
| 9000914 | 2/1990 | WIPO. |
| 9116945 | 11/1991 | WIPO. |
| 9119529 | 12/1991 | WIPO. |

Primary Examiner—Mark Bockelman
Attorney, Agent, or Firm—Lockwood, Alex, Fitzgibbon & Cummings

[57] ABSTRACT

A photodynamic therapy balloon catheter is provided which has an elongated light-emanating optical fiber, an inner tubular member, a balloon member surrounding the inner tubular member, and fluid material provided between the inner tubular member and the balloon member. Light-reflective material is included in any one or a plurality of the inner member, fluid material, and balloon member in any combination to provide a uniform illumination for activating treatment fluids located on an elongated treatment site within a living body.

29 Claims, 2 Drawing Sheets

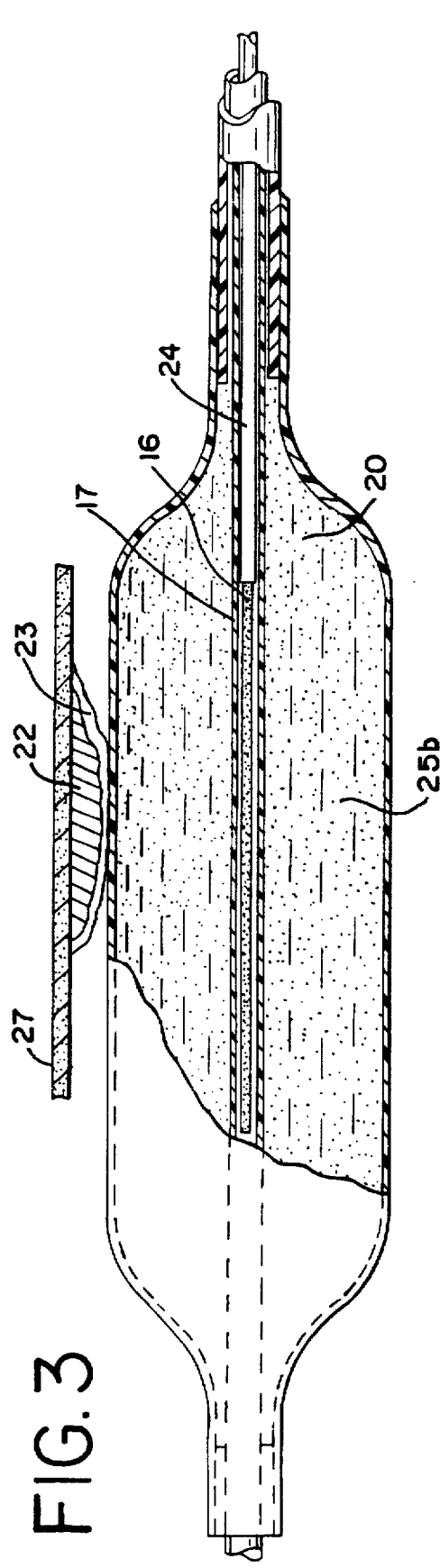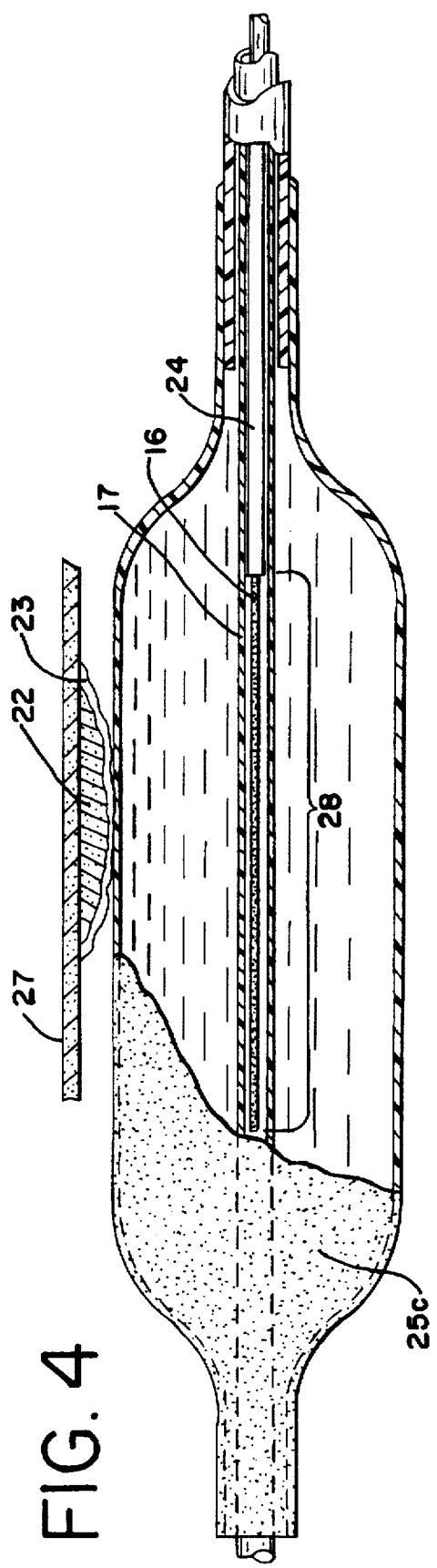

PHOTODYNAMIC THERAPY BALLOON CATHETER

BACKGROUND AND SUMMARY OF THE INVENTION

The present invention generally relates to medical catheters for activation of treatment fluids or medicaments at treatment sites within a living body. More particularly, the invention relates to photodynamic therapy balloon catheters which have optical features which more uniformly apply light energy in activating the treatment fluid at an in vivo treatment location.

Medicaments can be administered to living bodies by a number of approaches, including topical administration, intravenous administration, injection into body tissue via hypodermic needles and the like, and oral administration. In some instances, it is important to minimize the contact of the medicament with areas of the body other than the specific area targeted for treatment. For example, such an approach reduces the dilution effect by having to distribute the medicament to portions of the body that do not require the treatment. Direct delivery to the target site also minimizes the chance of side effects by restricting the drug administration to the precise site in need of treatment. In other instances, the area to be treated is not readily accessible in the absence of fully invasive surgery, such as when it is desired to treat the interior of a blood vessel or other body vessel or cavity.

Over the years, photodynamic catheters have been developed in order to provide for the activation of treatment fluids, medication, pharmaceuticals, drugs or other medicaments at a localized site. These are photodynamic components, and they do not become fully activated until they are illuminated with a prescribed light source, as generally known in the photodynamic medication art. This illumination must be of the inside of the vessel at the site being treated. Thus, photodynamic catheters have been proposed.

One difficulty that has been encountered in connection with photodynamic catheters for delivering the needed lumination is the lack of uniformity of light illuminating and activating the treatment fluids. In many photodynamic catheters, light is provided through an optical fiber to the distal end of the catheter. Typically this light is focussed or in a narrow or directed beam or beams, which can cause "hot spots" in the blood vessel or other internal organs. The "hot spots" typically result in uneven activation of the treatment fluid.

More particularly, photodynamic catheters can utilize optical fibers to provide light energy at the treatment site where the treatment fluid has been infused. A substantial shortcoming of these types of catheters can be the uneven illumination of the treatment fluid. As the photodynamic catheter is inserted through the body and positioned adjacent to the treatment site, the optical fiber transmits and provides a narrow beam of light at the treatment site through its distal tip. Since an optical fiber has cladding around its core, the light is directed through its length to its tip section. As the narrow beam of light emanates from the tip section of the optical fiber, it is more concentrated and longitudinally directed. Since the light emanates from the tip of the optical fiber and is longitudinally directed, it does not radiate efficiently in a radial direction perpendicular to the longitudinal axis of the optical fiber.

Moreover, since the tip of the optical fiber has a light emanating surface which is relatively short in the longitudinal direction, it does not illuminate simultaneously the entire surface area of the treatment fluid along the length of an elongated treatment location. As a result, different portions of the surface of the treatment fluid can be illuminated for different lengths of time, causing non-uniform activation of the photodynamic treatment fluid or medication. An approach which could be used to address this problem is to maneuver the photodynamic catheter in a forward and/or reverse direction, along the length of the treatment location, with a constant speed so that all of the photodynamic treatment fluid is illuminated with a same amount of light energy and for a same amount of time, providing a more even illumination of the entire surface of the treatment fluid. Such a maneuvering requirement becomes an additional variable which can detrimentally affect the reliability of the photodynamic catheterization procedure.

In accordance with the present invention, the undesirable aspects of "hot spots" and non-uniform light illumination of the treatment fluid is substantially eliminated. Instead, the light illumination of the treatment fluids is rendered uniform through the treatment length achieved by the present invention.

In summary, the present invention is a photodynamic therapy balloon catheter and procedure, wherein the catheter includes an elongated optical fiber light source which is cylindrically surrounded by a light-passing inner tubular member, a light-passing fluid, and a light-passing inflatable balloon member. At least one of the inner tubular member, fluid material, and/or balloon member includes light-reflection material or particles. Light emanating from the longitudinal optical fiber light source is reflected when it passes through the component containing the light-reflection material in order to provide a uniform illumination for activating treatment fluids at blood vessel walls or other internal organs.

It is a general object of the present invention to provide an improved photodynamic therapy balloon catheter and method of using same.

Another object of the present invention is to provide an improved photodynamic therapy balloon catheter that carries out localized treatment of internal body tissues.

Another object of this invention is to provide an improved photodynamic therapy balloon catheter which uses uniform light to illuminate and thus activate treatment fluids present on the walls of blood vessel or other internal organs.

Another object of the present invention is to provide an improved photodynamic therapy balloon catheter and procedure using optical principles to provide uniform light energy to treatment fluids at locations within the living body that are accessible through catheterization procedures.

Another object of the present invention is to provide an improved catheter and procedure which carries out localized treatment of internal body tissue, such as re-stenosis reduction and the treatment of cancers by localized activation of the treatment fluids at a tumor location for example.

BRIEF DESCRIPTION OF THE DRAWINGS

The invention will be further elucidated in the following description with reference to the drawings in which:

FIG. 3 is a detailed view shown in cross-section of the second embodiment of the catheter of this invention, illustrating the distal portion of the catheter shown in FIG. 1, located within a body vessel; and FIG. 4 is a detailed view shown in cross-section of the third embodiment of the catheter of this invention, illustrating the distal portion of the catheter shown in FIG. 1, located within a body vessel.

DESCRIPTION OF THE PARTICULAR EMBODIMENTS

Figures 1, 2:
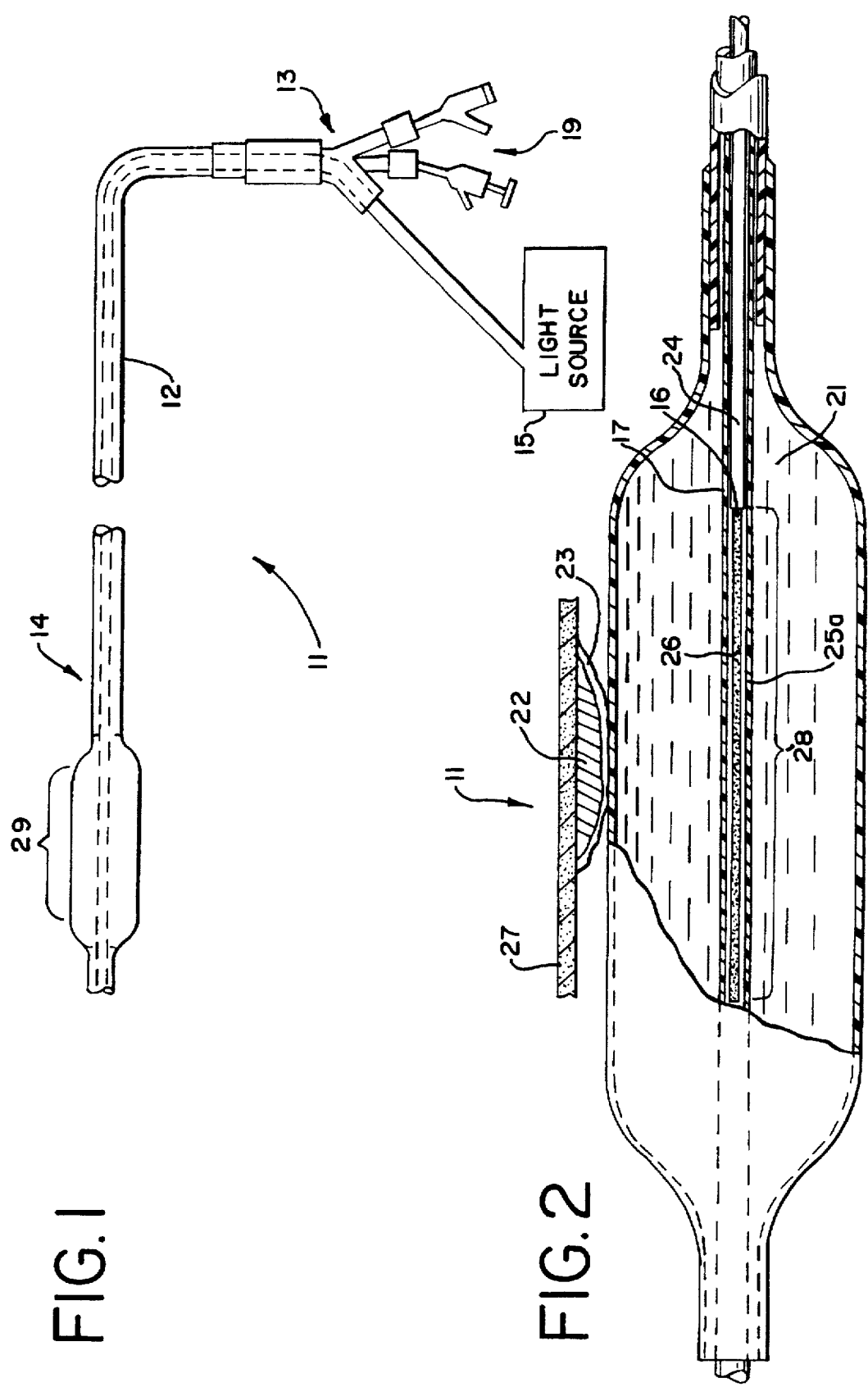
FIG. 1 is an elevational view, partially broken away, of a preferred photodynamic therapy balloon catheter in accordance with the present invention.
FIG. 2 is a detailed view shown in cross-section of the first embodiment of the catheter of this invention, illustrating the distal portion of the catheter shown in FIG. 1, located within a body vessel.

A photodynamic therapy balloon catheter, generally designated as 11, is generally illustrated in FIG. 1. The illustrated catheter includes a multilumen catheter tube 12, a proximal portion, generally designated as 13, and a distal portion generally designated as 14. Also included is a light transmission system including a light source 15.

As shown in FIG. 2, distal portion 14 includes an optical fiber 16. The optical fiber 16 is positioned interior to an inner tubular member 17. The inner member 17 is generally light-passing or optically clear. Typically, it will be made of a biocompatible polymer. Examples, include polyamides, polyurethanes, polyesters, polyolefins and the like. Specific examples include nylons, polyethylene, and the like. Suitable nylons include nylon 12, nylon 11, other nylon homopolymers and copolymers with other components. Grilamid (trademark) nylons and Vestamid (trademark) nylons are specific examples.

The inner member 17 is cylindrically surrounded by a generally light-passing inflatable balloon member 18. Balloon 18 is in fluid-passing communication with a lumen within the catheter tube. Balloon member 18 is also made of a biocompatible polymer and typically can be made of polymers of the type used in manufacturing the inner member 17. A fluid injector assembly 19, as shown in FIG. 1, of generally known construction passes inflation fluid through the lumen into the inflatable balloon member 18.

In the embodiment which is illustrated in greater detail in FIG. 2, balloon member 18 is shown in an inflated state and for engagement with an inside wall of a vessel 27 such as a blood vessel or the like. Description herein will be with respect to blood vessels; nevertheless, it will be understood that the invention is applicable to use with respect to other vessels or internal body components.

The balloon member 18 is inflated with generally light-passing or optically clear fluid material 20 such as saline solution or water. It will be appreciated that, with the balloon inflated as illustrated in FIG. 2, an annular chamber 21 is defined between the inner tubular member 17 and the balloon member 18. When the fluid material passes through the lumen, it enters into annular chamber 21, causing balloon member 18 to open up and move toward contact with the vessel wall 27.

According to the present invention, in order to activate a photodynamic treatment fluid 23 (discussed in greater detail herein) more effectively, it must be illuminated more evenly and uniformly. To uniformly and efficiently illuminate the photodynamic treatment fluid 23, cladding material 24 on the optical fiber 16 is removed at its distal portion, exposing an optical fiber core 26. By removing cladding material 24, an elongated light emanating area 28 is provided. The length of area 28 approximates the working length 29 of balloon member 18. The illuminating light from the elongated light-emanating area 28 radiates in a perpendicular or radial direction in relation to the longitudinal axis of the optical fiber core 26. This perpendicular or radial radiation of the illuminating light provides a cylindrical illumination pattern extending over the working area 29 of the balloon and the entire surface area of the treatment fluid 23, including its entire longitudinal extent.

Furthermore, in order to achieve an even more uniformly lit area, the optical fiber core 26 can be tapered such that it has a reducing thickness in the distal direction. Alternatively, any cladding remaining in the elongated area 28 could be tapered in the same direction. A gradient reduction in the thickness of the optical fiber component provides for the light which emanates along the length of the elongated light-emanating area 28 to illuminate with a higher degree of uniformity. The intensity of the light energy present in the optical fiber core 26 decreases in the distal direction, due to the greater longitudinal distance through which the light must pass at the more distal portions of the optical fiber. By the tapering effect and the reduction in the thickness in the distal direction, the more distal portions have a shorter radial distance through which to pass. Thus, the greater longitudinal distances are combined with the shorter radial distances, and vice versa, to achieve a total light path (longitudinal plus radial) which is about the same throughout the light-emanating area, which allows the light energy emanating from the core 26 to be more uniform.

When included, the tapering of the optical fiber component can be effected through chemical etching or physical abrasion. It is further understood that the physical abrasion can be accomplished by using a gritty surface such as sand paper to longitudinally abrade the surface of the optical fiber component, whether such is carried out in a distally tapering or a right-cylindrical pattern.

To further achieve a greater degree of light illumination uniformity in accordance with the invention, highly reflective material or particles are compounded with the inner member 17, fluid material 20, and/or balloon member 18. As the light encounters the highly reflective material, it reflects in different directions producing a uniform glow. This addition of the highly reflective particles to the above-mentioned elements results in the scattering and dispersing of the light, thereby uniformly lighting the cylindrical elongated light-emanating area 28 and the treatment fluid infused at the treatment site.

In the first embodiment as illustrated in FIG. 2, reflective material 25a is in the form of particles compounded with the inner tubular member 17 such that light passing through the inner tubular member will be reflected by the reflective particles 25a. Either these particles can be loaded into the polymer such as at extrusion of the inner member 17, or they can be coated onto one or both of the surfaces of the tubular member. Suitable reflective material includes titanium dioxide ($TiO_2$) and silver, with titanium dioxide being preferred. The presence of the reflective material causes the light emanating from the optical fiber to reflect and disperse at least along the entire length of the light-emanating area 28, producing a uniform cylindrically-shaped ring of illumination that delivers the light energy uniformly along the length of the vessel or the like at which photodynamic treatment fluid is located. The uniform light has the desirable effect of eliminating light energy "hot spots" and uneven activation of the treatment fluid.

The second embodiment of the present invention, illustrated in FIG. 3, calls for the presence of the reflective material 25b in the fluid material 20. Reflective material 25b is in the form of particulates suspended within the fluid material 20, resulting in the reflection off of these particles of the light emanating from the optical fiber 16. It will be noted that the thus reflective fluid filled within the annular chamber 21 fully surrounds the light-emanating area and provides a depth of reflective particles in the fluid through which the light must pass along its path to the balloon 18 and hence to the vessel wall. Reflection off the particles and the resulting light dispersion produces a uniform light having the previously mentioned desirable effects of eliminating the uneven activation of the treatment fluid which is generally along the outside surface of the balloon member 18.

The third embodiment, illustrated in FIG. 4, is the preferred embodiment of the present invention and is generally similar to that of FIG. 2. In this embodiment the reflective material 25c is in the nature of highly reflective particles compounded with the material of the balloon member 18, for example either coated on the balloon member 18 or loaded into the polymer out of which the balloon member 18 is constructed. It will be appreciated that the loading is accomplished during the extrusion of the parison from which balloon member 18 is subsequently formed. The presence of the reflective material produces a reflecting and scattering effect. The inner tubular member 17 and the fluid material 20 in this embodiment are light-passing in order to allow light transmission from the optical fiber 16. As the light encounters the balloon member 18, the reflective particles 25c integrate the light along at least the treatment length and transmit a portion of the light energy to the vessel wall to be treated. This allows the light to be more uniform and even as it is transmitted through the balloon wall creating an even distribution of light energy to activate the treatment fluid 23 (photodynamic substance) already infused in or otherwise dispersed to the vessel wall, especially to the diseased area 22.

When the reflective particles are compounded with the polymer out of which the inner tubular member and/or the balloon member are constructed, the amount of compounding can be between about 5 and about 40 weight percent reflective material based on the total weight of the polymer. It is preferred that this ratio be in the range of about 10 to about 40 weight percent, most preferably between about 25 and about 35 percent by weight of the total weight of the polymer. An alternative approach for compounding the balloon member 18 or the inner member 17 with the reflective particles includes coextruding or otherwise positioning a layer of highly reflective material or particles between two layers of polymer. It has been noted that 90% light illumination uniformity can be achieved when compounding the fluid material 20 and/or balloon member 18 with the highly reflective material 25b or 25c, respectively.

With more particular reference to the light dissipation achieved, especially in the third embodiment, the light is integrated before it emanates from the balloon member 18 into the vessel wall. By rendering the balloon material semi-reflective and semi-transparent, one can achieve more uniformity along the cylindrical surface of the balloon, thereby optimizing the delivery of light to the treatment fluid 23 which has been absorbed into the vessel wall to be treated.

In the above embodiments, coating of the inner member 17 or balloon member 18 can be achieved by known methods such as evaporation, sputtering, or ion bombardment of the reflective material. Such coating can be on the inside, the outside, or both the inside and outside of the inner member 17 or balloon member 18.

In the present invention the reflective material can be included in any one or a plurality of the inner member 17, balloon member 18, and fluid material 20, in any combination. By adding the reflective material in these different combinations, it is possible to tailor the reflectivity and uniformity of light illumination to fit a particular need or a criterion for activating any of various photodynamic medicaments and the like.

It will be understood that the embodiments of the present invention which have been described are illustrative of some of applications of the principles of the present invention. Various modifications may be made by those skilled in the art without departing from the true spirit and scope of the invention.

I claim:

1. A photodynamic therapy balloon catheter for activating treatment fluid at a location within a living body, comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber, said inner tubular member being made of a polymer material;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member, said balloon member being made of a polymeric material;

a light source communicating with said optical fiber to deliver light energy to said light energy emanating section; and at least one of said inner tubular member and said balloon member includes light-reflective material which, upon light emanating through the light energy emanating section, reflects said light energy and activates photodynamic treatment fluid at a location within a living body, said light-reflective material being loaded into said polymer material from which said at least one of said inner tubular member and said balloon member is made.

2. The photodynamic catheter of claim 1, wherein said light-reflective material is present in a quantity so as to disperse the light energy and produce a uniform illumination of light.

3. The photodynamic catheter of claim 1, wherein said generally distal light energy emanating section extends longitudinally for a distance approximating the length of a cylindrical working surface of the balloon member.

4. The photodynamic catheter of claim 1, wherein said optical fiber is tapered such that said optical fiber decreases in thickness in the distal direction, and wherein the light emanating from said light energy emanating section of said optical fiber is a uniformly illuminating light.

5. The photodynamic therapy balloon catheter of claim 1, wherein said inner tubular member is coated with reflective material.

6. The photodynamic therapy balloon catheter of claim 5, wherein said reflective material is $TiO_2$.

7. The photodynamic therapy balloon catheter of claim 1, wherein said balloon member is coated with reflective material.

8. The photodynamic therapy balloon catheter of claim 7, wherein said reflective material is TiO$_2$.

9. The photodynamic therapy balloon catheter of claim 1, wherein said reflective material is TiO$_2$.

10. The photodynamic therapy balloon catheter of claim 1, wherein the loaded reflective material is from about 5 to about 40 percent by weight of the total weight of the inner tubular member.

11. A photodynamic therapy balloon catheter for activating treatment fluid at a location within a living body, comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light source communicating with said optical fiber to deliver light energy to said light energy emanating section; and said balloon member includes light-reflective material which, upon light emanating through the light energy emanating section, reflects said light energy and activates photodynamic treatment fluid at a location within a living body, and said balloon member is loaded with said reflective material.

12. The photodynamic therapy balloon catheter of claim 1, wherein said reflective material is TiO$_2$.

13. The photodynamic therapy balloon catheter of claim 11, wherein the loaded reflective material is from about 5 to 40 percent by weight of the total weight of the balloon member.

14. The photodynamic therapy balloon catheter of claim 13, wherein the loaded reflective material is from about 10 to about 40 percent by weight of the total weight of the balloon member.

15. A photodynamic therapy balloon catheter for activating treatment fluid at a location within a living body, the catheter comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light-passing fluid material positioned between said inner tubular member and said inflatable balloon member;

a light source communicating with said optical fiber to deliver light energy to said light energy emanating section; and at least one of said inner tubular member and said balloon member includes light-reflective material and which, upon light emanating through the light energy emanating section, reflects said light energy and activates photodynamic treatment fluid at a location within a living body, and said at least one of said inner tubular member and said balloon member is made of a polymer loaded with said reflective material.

16. The photodynamic therapy balloon catheter of claim 15, wherein said at least one of the inner tubular member and the balloon member is coated with reflective material.

17. The photodynamic therapy balloon catheter of claim 16, wherein said reflective material is TiO$_2$.

18. The photodynamic therapy balloon catheter of claim 15, wherein said reflective material is TiO$_2$.

19. The photodynamic therapy balloon catheter of claim 15, wherein the loaded reflective material is from about 5 to 40 percent by weight of the total weight of the balloon member.

20. The photodynamic therapy balloon catheter of claim 19, wherein the loaded reflective material is from about 10 to 40 percent by weight of the total weight of the balloon member.

21. The photodynamic therapy balloon catheter of claim 15, wherein said fluid material contains reflective material.

22. The photodynamic therapy balloon catheter of claim 21, wherein said reflective material is TiO$_2$.

23. The photodynamic therapy balloon catheter of claim 15, wherein the loaded reflective material is from about 5 to about 40 percent by weight of the total weight of the inner tubular member.

24. A photodynamic therapy balloon catheter for activating treatment fluid at a location within a living body, the catheter comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light-passing fluid material positioned between said inner tubular member and said inflatable balloon member;

a light source communicating with said optical fiber to deliver light energy to said light energy emanating section; and said balloon member includes light-reflective material and which, upon light emanating through the light energy emanating section, reflects said light energy and activates photodynamic treatment fluid at a location within a living body, and said balloon member is coextruded with reflective material such that said reflective material is positioned between an inner wall and an outer wall of said balloon member.

25. The photodynamic therapy balloon catheter of claim 24, wherein said at least one of the inner tubular member and the balloon member is coated with reflective material.

26. The photodynamic therapy balloon catheter of claim 25, wherein said reflective material is $TiO_2$.

27. A photodynamic therapy balloon catheter for activating treatment fluid at a location within a living body, the catheter comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light-passing fluid material positioned between said inner tubular member and said inflatable balloon member;

a light source communicating with said optical fiber to deliver light energy to said light energy emanating section; and at least one of said inner tubular member and said balloon member includes light-reflective material and which, upon light emanating through the light energy emanating section, reflects said light energy and activates photodynamic treatment fluid at a location within a living body, said at least one of the inner tubular member and the balloon member being made of a polymer loaded with reflective material, and the loaded reflective material is from about 10 to about 40 percent by weight of the total weight of the member.

28. A photodynamic therapy balloon catheter for activating treatment fluid at a location within a living body, comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light source communicating with said optical fiber to deliver light energy to said light energy emanating section; and said balloon member includes light-reflective material which, upon light emanating through the light energy emanating section, reflects said light energy and activates photodynamic treatment fluid at a location within a living body, and the balloon member is coextruded with reflective material such that said reflective material is positioned between an inner wall and an outer wall of said balloon member.

29. A photodynamic therapy balloon catheter for activating treatment fluid at a location within a living body, comprising:

an elongated tubular catheter having a proximal portion which remains outside of the living body when in use, the catheter also having a distal portion which is inserted into the living body when in use;

an optical fiber extending along the length of said catheter, said optical fiber having a generally distal light energy emanating section;

said elongated tubular catheter having a light-passing inner tubular member cylindrically surrounding said optical fiber and extending longitudinally along the length of the light energy emanating section of said optical fiber;

a light-passing inflatable balloon member at said distal portion of the catheter, said balloon member being in fluid-passing communication with said proximal portion of the catheter, said balloon member cylindrically surrounding said inner tubular member and extending longitudinally with respect to said inner tubular member;

a light source communicating with said optical fiber to deliver light energy to said light energy emanating section; and said inner tubular member includes light-reflective material which, upon light emanating through the light energy emanating section, reflects said light energy and activates photodynamic treatment fluid at a location within a living body, and said inner tubular member being loaded with reflective material, and the loaded reflective material is from about 10 to about 40 percent by weight of the total weight of the inner tubular member.

* * * * *

UNITED STATES PATENT AND TRADEMARK OFFICE
CERTIFICATE OF CORRECTION

PATENT NO. : 5,797,868
DATED : Aug. 25, 1998
INVENTOR(S) : James E. Leone

It is certified that error appears in the above-identified patent and that said Letters Patent is hereby corrected as shown below:

Col. 1, lines 41-42, "lumination" should read --illumination--.
Col. 6, line 8, "of applications" should read --of the applications--.
Col. 7, claim 12, line 44, "1," should read --11,--.

Signed and Sealed this

First Day of December, 1998

Attest:

BRUCE LEHMAN

*Attesting Officer*     *Commissioner of Patents and Trademarks*